United States Patent [19]

Bormann et al.

[11] Patent Number: 5,061,703
[45] Date of Patent: Oct. 29, 1991

[54] ADAMANTANE DERIVATIVES IN THE PREVENTION AND TREATMENT OF CEREBRAL ISCHEMIA

[75] Inventors: Joachim Bormann, Frankfurt; Markus R. Gold, Nauheim; Wolfgang Schatton, Eschborn, all of Fed. Rep. of Germany

[73] Assignee: Merz + Co. GmbH & Co., Frankfurt am Main, Fed. Rep. of Germany

[21] Appl. No.: 508,109

[22] Filed: Apr. 11, 1990

[30] Foreign Application Priority Data

Apr. 14, 1989 [EP] European Pat. Off. ........... 89106657

[51] Int. Cl.$^5$ ..................... A61K 31/13; A61K 31/41; A61K 31/55; A61K 31/445
[52] U.S. Cl. .................................. 514/212; 514/325; 514/359; 514/662
[58] Field of Search ................ 514/212, 325, 359, 662

[56] References Cited

FOREIGN PATENT DOCUMENTS 0227410 7/1987 European Pat. Off. .

OTHER PUBLICATIONS

Marcy, R. et al.; J. Pharmacol. 13 (1), pp. 163-164 (1982).
Miura, Y. et al.; Japan. J. Pharmacol. 39, pp. 443-451 (1986).
Miltner, F. O.; Arzneimittelforschung. 32 (10), pp. 1268-1270 (1982).
Miltner, F. O.; Arzneimittelforschung. 32 (10), pp. 1271-1273 (1982).
Hamoen, A. M.; British Medical Journal. 3, (5874), pp. 272-273 (1973).
Kinomota, H. et al.; No Skinkei Geka, 12 (1), pp. 37-45 (1984).
Otomo, E; Japan. J. Neuropsychopharmacol. 4/2, pp. 113-119 (1982).
Berkow, R.; The Merck Manual. 15, pp. 1336-1340 (1987).
Krieglstein, J., Weber, J. in Oxygen Transport to Tissue, VIII, Longmuir, I. S., Editor; Plenum Publishing Corporation; pp. 243-253 (1986).
Sugio, K. et al.; Japan. J. Pharmacol. 47, pp. 327-329 (1988).
Hossman, K. A.; Critical Care Medicine. 16 (10), pp. 964-971 (1988).
Hoyer, S.; Aging. 11, pp. 158-166 (1988).

Primary Examiner—Stanley J. Friedman
Attorney, Agent, or Firm—Gordon W. Hueschen

[57] ABSTRACT

A method for the prevention and treatment of cerebral ischemia using an adamantane derivative of the formula

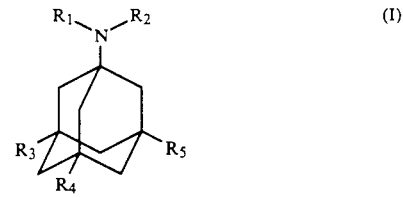

wherein $R_1$ and $R_2$ are identical or different, representing hydrogen or a straight or branched alkyl group of 1 to 6 C atoms or, in conjunction with N, a heterocyclic group with 5 or 6 ring C atoms;

wherein $R_3$ and $R_4$ are identical or different, being selected from hydrogen, a straight or branched alkyl group of 1 to 6 C atoms, a cycloalkyl group with 5 or 6 C atoms, and phenyl;

wherein $R_5$ is hydrogen or a straight or branched $C_1$-$C_6$ alkyl group, or a pharmaceutically-acceptable salt thereof, is disclosed.

13 Claims, No Drawings

ADAMANTANE DERIVATIVES IN THE PREVENTION AND TREATMENT OF CEREBRAL ISCHEMIA

The present invention relates to a method for the prevention or treatment of cerebral ischemia using an adamantane derivative of the following general formula

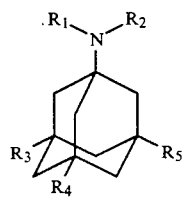

wherein
$R_1$ and $R_2$ are identical or different and represent hydrogen or a straight or branched alkyl group of 1 to 6 C atoms or, in conjunction with N, a heterocyclic radical with 5 or 6 ring C atoms;
wherein
$R_3$ and $R_4$ are identical or different, being selected from hydrogen, a straight or branched alkyl group of 1 to 6 C atoms, a cycloalkyl group with 5 or 6 C atoms, and phenyl; and
wherein
$R_5$ is hydrogen or a straight or branched $C_1$–$C_6$ alkyl group, or a pharmaceutically-acceptable acid addition salt thereof. Herein branched or straight $C_1$–$C_6$ alkyl groups representatively include methyl, ethyl, iso- and n-propyl, n-, iso- and t-butyl, n-pentyl, n-hexyl, and the isomers thereof.

Certain 1-amino adamantanes of formula (I) are known. 1-amino-3,5-dimethyl adamantane, for example, is the subject matter of German patents 22 19 256 and 28 56 393.

Some 3,5-disubstituted 1-amino adamantanes of formula (I) are described in U.S. Pat. No. 4,122,193. 1-amino-3-ethyl adamantane is described in German Patent 22 32 735.

The compounds of formula (I) are generally prepared by alkylation of halogenated adamantanes, preferably bromo- or chloroadamantanes. The di- or tri-substituted adamantanes are obtained by additional halogenation and alkylation procedures. The amino group is introduced either by oxidation with chromiumtrioxide and bromination with HBr or bromination with bromine and reaction with formamide followed by hydrolysis. The amino function can be alkylated according to generally-accepted methods. Methylation can, for example, be effected by reaction with chloromethyl formate and subsequent reduction. The ethyl group can be introduced by reduction of the respective acetamide.

In accordance with U.S. Pat. No. 4,122,193 amination can also be effected by reaction of the respective 1-halogen-3,5- or -7-substituted adamantane with a urea derivative of the formula

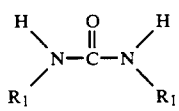

wherein $R_1$ is hydrogen or alkyl.

The compounds according to formula (I) are prepared according to the following reaction scheme:

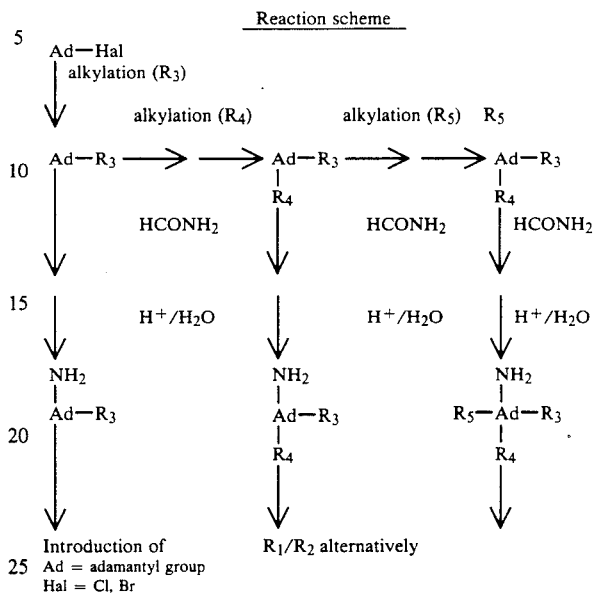

Alkylation of the halogenated adamantanes can be achieved by known methods, for example, through Friedel-Crafts reaction (introduction of phenyl group), or by reaction with vinylidene chloride, subsequent reduction and suitable Wittig reaction of the aldehydes and subsequent hydration, or by introduction of ethylene and subsequent alkylation with appropriate cuprates, or by introduction of ethylene and reduction of the halogen alkyl adamantanes, or by acylation with $CO_2$ and reduction of the carboxylic acid.

The compounds according to formula (I) known from the above-cited patents have so far been used for the treatment of parkinsonian and parkinsonoid diseases. Their mode of action is attributed to a dopaminergic influence on the CNS, either by an increased release of the transmitter substance dopamine or by an inhibition of its uptake. This compensates the imbalance of the dopamine/acetylcholine system.

In contrast to this type of disease, cerebral ischemia is characterized by a pathophysiological situation defined by an imbalance of neuronal stimulation mechanisms. In this context, the excessive inflow of calcium through NMDA receptor channels finally leads to the destruction of brain cells in specific brain areas (Rothmann & Olney, Trends Neurosci 10, 1989, pp. 299).

Therefore, in order to treat or eliminate this pathological situation, an antagonistic intervention is required with regard to the NMDA receptor channels (Kemp et al., Trends Pharmacol., Sci. 8, 1987. pp. 414).

Such intervention can, for example, be effected using substituted fluoro and hydroxy derivatives of dibenzo-[a,d]-cyclo-heptene-5,10-imine which are described in EP-A 0 264 183.

These heterocyclic, aromatic compounds are lipophilic and exhibit NMDA receptor channel-antagonistic and anticonvulsive properties. They are prepared by a relatively expensive method generating enantiomer mixtures which may be split into the individual optical antipodes.

The present invention is aimed at preparing and employing compounds which can be chemically generated by simple methods, exhibiting an NMDA receptor channel-antagonistic and anticonvulsive action, for use in the prevention and treatment of cerebral ischemia.

This objective can be achieved according to the invention by using the 1-amino adamantanes of formula (I).

It has been found unexpectedly that the use of these compounds prevents an impairment or further impairment, i.e., degeneration and loss of nerve cells, after ischemia. Therefore, the adamantane derivatives of formula (I) are especially suited for the prevention and treatment of cerebral ischemia after apoplexy, open-heart surgery, cardiac standstill, subarachnoidal homorrhage, transient cerebro-ischemic attacks, perinatal asphyxia, anoxia, hypoglycemia, apnoea and Alzheimer's disease. The amount employed is a cerebral ischemia-alleviating or preventive amount.

Examples of compounds prepared and used according to the invention are:
1-amino adamantane
1-amino-3-phenyl adamantane
1-amino-methyl-adamantane
1-amino-3,5-dimethyl adamantane (test compound no. 1)
1-amino-3-ethyl adamantane (test compound no. 2)
1-amino-3-isopropyl adamantane (test compound no. 3)
1-amino-3-n-butyl adamantane
1-amino-3,5-diethyl adamantane (test compound no. 4)
1-amino-3,5-diisopropyl adamantane
1-amino-3,5-di-n-butyl adamantane
1-amino-3-methyl-5-ethyl adamantane
1-N-methylamino-3,5-dimethyl adamantane (test compound no. 5)
1-N-ethylamino-3,5-dimethyl adamantane (test compound no. 6)
1-N-isopropyl-amino-3,5-dimethyl adamantane
1-N,N-dimethyl-amino-3,5-dimethyl adamantane
1-N-methyl-N-isopropyl-amino-3-methyl-5-ethyl adamantane
1-amino-3-butyl-5-phenyl adamantane
1-amino-3-pentyl adamantane
1-amino-3,5-dipentyl adamantane
1-amino-3-pentyl-5-hexyl adamantane
1-amino-3-pentyl-5-cyclohexyl adamantane
1-amino-3-pentyl-5-phenyl adamantane
1-amino-3-hexyl adamantane
1-amino-3,5-dihexyl adamantane
1-amino-3-hexyl-5-cyclohexyl adamantane
1-amino-3-hexyl-5-phenyl adamantane
1-amino-3-cyclohexyl adamantane (test compound no. 7)
1-amino-3,5-dicyclohexyl adamantane
1-amino-3-cyclohexyl-5-phenyl adamantane
1-amino-3,5-diphenyl adamantane
1-amino-3,5,7-trimethyl adamantane
1-amino-3,5-dimethyl-7-ethyl adamantane (test compound no. 8)
1-amino-3,5-diethyl-7-methyl adamantane
1-N-pyrrolidino and 1-N-piperidine derivatives,
1-amino-3-methyl-5-propyl adamantane
1-amino-3-methyl-5-butyl adamantane
1-amino-3-methyl-5-pentyl adamantane
1-amino-3-methyl-5-hexyl adamantane
1-amino-3-methyl-5-cyclohexyl adamantane
1-amino-3-methyl-5-phenyl adamantane
1-amino-3-ethyl-5-propyl adamantane
1-amino-3-ethyl-5-butyl adamantane
1-amino-3-ethyl-5-pentyl adamantane
1-amino-3-ethyl-5-hexyl adamantane
1-amino-3-ethyl-5-cyclohexyl adamantane
1-amino-3-ethyl-5-phenyl adamantane
1-amino-3-propyl-5-butyl adamantane
1-amino-3-propyl-5-pentyl adamantane
1-amino-3-propyl-5-hexyl adamantane
1-amino-3-propyl-5-cyclohexyl adamantane
1-amino-3-propyl-5-phenyl adamantane
1-amino-3-butyl-5-pentyl adamantane
1-amino-3-butyl-5-hexyl adamantane
1-amino-3-butyl-5-cyclohexyl adamantane
their N-methyl, N,N-dimethyl, N-ethyl, N-propyl derivatives and their acid addition compounds.

Preferred compounds of formula (I) are those wherein $R_1$ and $R_2$ are hydrogen such as, for example, 1-amino-3-ethyl-5,7-dimethyl adamantane, and compounds wherein $R_1$, $R_2$, $R_4$ and $R_5$ are hydrogen such as, for example, 1-amino-3-cyclohexyl adamantane and 1-amino-3-ethyl adamantane.

Additional preferred compounds are those wherein $R_1$, $R_2$ and $R_5$ are hydrogen such as, for example, 1-amino-3-methyl-5-propyl or 5-butyl adamantane, 1-amino-3-methyl-5-hexyl or cyclohexyl adamantane, or 1-amino-3-methyl-5-phenyl adamantane.

Especially preferred compounds are 1-amino-3,5-dimethyl adamantane, 1-amino-3,5-diethyl adamantane, i.e., compounds wherein $R_1$, $R_2$ and $R_5$ are hydrogen, and compounds wherein $R_1$ and $R_5$ are hydrogen, $R_2$ is methyl or ethyl, and $R_3$ and $R_4$ are methyl such as, for example, 1-N-methylamino-3,5-dimethyl adamantane and 1-N-ethylamino-3,5-dimethyl adamantane.

The adamantane derivatives of formula (I) may be applied as such or in the form of their pharmaceutically-acceptable acid addition salts including, for example, the hydrochlorides, hydrobromides, sulfates, acetates, succinates or tartrates, or their acid addition salts with fumaric, maleic, citric, or phosphoric acids.

The compounds of formula (I) are administered in suitable form in doses ranging from about 0.01 to 100 mg/kg. Appropriate presentation forms are, for example, combinations of the active substance with common pharmaceutical carriers and adjuvants in the form of tablets, coated tablets, and sterile solutions or suspensions for injection. Pharmaceutically-acceptable carriers are, for example, lactose, sucrose, sorbitol, talc, stearic acid, magnesium stearate, gum arabic, corn starch, or cellulose, combined with diluents such as water, polyethylene glycol, etc. Solid presentation forms are prepared according to common methods and may contain up to 50 mg of the active ingredient per unit.

The efficacy of the compounds of formula (I) is described in the following pharmacological tests.

A. Displacement of TCP Binding

Phencyclidine (PCP), a known NMDA antagonist, binds to the NMDA receptor-associated ionic channel and blocks ionic transport (Garthwaite & Garthwaite, Neurosci. Lett. 83, 1987, 241–246). Additionally, PCP has been shown to prevent the destruction of brain cells after cerebral ischemia in rats (Sauer et al., Neurosci. Lett. 91, 1988, 327–332).

The interaction between compounds of formula (I) and the PCP bond is studied in the following. In this test $^3$H-TCP, a PCP analogue, is used.

A membrane preparation of rat cortex is incubated with $^3$H-TCP which is an analogue of phencyclidine (PCP) (Quirion & Pert 1982, Eur. J. Pharmacol. 83:155).

The interaction with the TCP binding is assessed for test compound no. 1 (1-amino-3,5-dimethyl adamantane) in a competitive experiment. This test shows that compound no. 1 is very effective in displacing TCP from the bond. The $IC_{50}$ value is 89 nM. The conclusion can be drawn that compound no. 1 binds to NMDA receptor channels at the same site as the NMDA antagonist PCP.

B. Blocking of NMDA Receptor Channels

In the following test it is shown that the compounds of formula (I) according to the invention are as effective as PCP in blocking the NMDA receptor channel.

In the patch-clamp experiment, the current flowing through NMDA-activated membrane channels of cultivated spinal marrow neurons (mouse) is measured (Hamill et al 1981, Pflügers Arch. 312: 85–100). After application of 20 μM NMDA, the current signal of the cell is integrated for 20 sec. and recorded as a control answer ($A_c$). During succeeding application of 20 μM NMDA and 6 μM of an adamantane derivative, the intensity of the substance effect can be determined as a relative change of the control answer ($A/A_c - A =$ test answer).

The results are summarized in the following Table 1:

TABLE 1

| Compound no. | 1-A/Ac | n |
|---|---|---|
| 1 | 0.66 ± 0.05 | 14 |
| 2 | 0.44 ± 0.08 | 7 |
| 3 | 0.58 ± 0.07 | 7 |
| 4 | 0.50 ± 0.11 | 5 |
| 5 | 0.56 ± 0.07 | 7 |
| 6 | 0.38 ± 0.05 | 7 |
| 7 | 0.25 ± 0.04 | 11 |
| 8 | 0.50 ± 0.03 | 6 |
| PCP | 0.50 ± 0.04 | 7 |
| MK-801 | 0.60 ± 0.05 | 22 |

The values are given as means ± SEM.

As can be seen from the results, the aminoadamantane derivatives of formula (I) are able to block the NMDA receptor channel as has been described for PCP (Bertolini et al., Neurosci. Lett. 84, 1988, 351–355) and for 5-methyl-10,11-dihydro-5H-dibenzo[a,d]cycloheptene-5,10-imine (MK-801) (EP-A 0 264 183).

C. Anticonvulsive Effect 4, 12, 36, 108 and 324 mg/kg of the test substance is administered to mice by the intraperitoneal route (5 animals per dose). The supermaximum electroshock test is applied forty (40) minutes after application of the substance to investigate the anti-convulsive potential of the substance. The protected animals are added up over all dosages (score; maximum = 25 animals).

The results are given in the following Table 2.

TABLE 2

| Compound no. | Anticonvulsive action (score) | Mean | $ED_{50}$ (mg/kg) |
|---|---|---|---|
| 1 | 18 | | |
| | 16 | | |
| | 16 | | |
| | 15 | 16.3 | 16 |
| 2 | 15 | | |
| | 14 | | |
| | 12 | 13.7 | 30 |
| 4 | 16 | | |
| | 16 | | |
| | 11 | 14.3 | 24 |
| 5 | 17 | | |

TABLE 2-continued

| Compound no. | Anticonvulsive action (score) | Mean | $ED_{50}$ (mg/kg) |
|---|---|---|---|
| | 17 | 17.0 | 13 |
| Standards: | | | |
| PCP | 19 | 19.0 | 9 |
| MK-801 | 25 | 25.0 | <1 |

The $ED_{50}$ values were estimated according to Litchfield, J. T. and Wilcoxon, F., J. Pharmacol. Exp. Therap. 96, 99–113 (1949).

As can be seen from the above results, aminoadamantane derivatives of formula (I) exhibit a protective effect against electrically induced convulsions. They therefore have an anticonvulsive effect.

D. Correlation Between Channel-Blocking and Anticonvulsive Action

The correlation between the action of the tested adamantane derivatives 1–8 at the NMDA receptor channel (in vitro) and the anticonvulsive effect (in vivo) has been tested. For this purpose an xy diagram of both test parameters is plotted. It shows that there is a correlation between the blocking of the NMDA receptor channel and the anticonvulsive action of the adamantanes of formula (I).

E. Protection Against Cerebral Ischemia

Both carotid arteries are occluded in rats for 10 minutes. At the same time the blood pressure is reduced to 60–80 mg Hg by withdrawal of blood (Smith et al. 1984, Acta Neurol. Scand. 69: 385, 401). The ischemia is terminated by opening the carotids and reinfusion of the withdrawn blood. After seven days the brains of the test animals are histologically examined for cellular changes in the CA1–CA4 region of the hippocampus, and the percentage of destroyed neurons is determined. The action of test compound No. 1 is determined after a single administration of 5 mg/kg and 20 mg/kg one (1) hour prior to the ischemia.

The results are summarized in the following Table 3:

TABLE 3

| | | Test compound no. 1 | |
|---|---|---|---|
| Area | Control | 5 mg/kg (n = 5) | 20 mg/kg (n = 6) |
| CA1 | 80.2 ± 1.5 | 83.0 ± 2.2 | 53.1 ± 6.1** |
| CA3 | 3.6 ± 1.1 | 7.3 ± 1.8 | 2.7 ± 1.0 |
| CA4 | 1.4 ± 0.4 | 3.7 ± 1.7 | 0.6 ± 0.3 |

The values are given in percent of damaged neurons ± SEM.
Significance of the mean difference: **p < 0.01 (U test)

The results show that the reduction of the post-ischemic neuronal brain damage in the CA1 region of the rat hippocampus is statistically significant after the pre-ischemic application of 20 mg/kg of test compound no. 1. Physiological parameters (e.g. blood pressure, body temperature) are not affected by the treatment. Moreover, the results show that the compounds according to formula (I) exhibit a neuroprotective action in cerebral ischemia.

Essentially the same result is attained by employing the compounds of the other Examples, especially those designated test compounds 2–8.

F. Protection Against NMDA-Induced Mortality

It is well known that, subsequent to cerebral ischemia, glutamate and aspartate levels increase massively in the brain. These excitatory aminoacids overstimulate the NMDA-subtype of the glutamate receptor thus leading to delayed neuronal death. A similar pathophysiological situation is obtained when mice are administered intraperitoneally with 200 mg/kg NMDA. This high dose will eventually cause 100% mortality in the animals (Leander et al. 1984, Brain Res. 448; 115-120). We have found that the adamantane derivatives of the present invention are protective against the NMDA-induced mortality.

| Compound No. | Dose mg/kg | Protected Animals |
|---|---|---|
| 1 | 50 | 8/8 |
|   | 25 | 6/8 |
|   | 10 | 3/8 |
| 3 | 50 | 6/8 |
|   | 25 | 4/8 |
| 4 | 50 | 7/8 |
|   | 25 | 5/8 |
| 5 | 25 | 5/8 |

In the control animals, to which no adamantane was administered, the mortality was eight (8) animals out of eight (8).

G. Displacement of [$^3$H] MK-801 Binding in Human Brain Tissue

MK-801 binds to the ion channel associated with the NMDA receptor, as well as TCP does. This binding site is thought to mediate the neuroprotective effects of non-competitive NMDA-antagonists.

We have investigated whether the adamantane derivatives of the present invention are active at the MK-801 binding site. Tissue from frontal cortex was taken from patients at autopsy and homogenates were prepared. Inhibition of specific [$^3$H] MK-801 binding (3 nM) by the test compounds was determined (see e.g. Kornhuber et al. 1989, Eur. J. Pharmacol. 166: 589-590).

The test compounds were highly potent in displacing MK-801 binding, thus indicating a specific interaction with the NMDA receptor channel and predicting neuroprotective properties.

| Compound No. | Ki nM |
|---|---|
| 1 | 536 |
| 3 | 598 |
| 4 | 189 |
| 5 | 1607 | wherein $K_i$ is the inhibition constant and nM is nanomoles per liter. Mean values from triplicate experiments are given ± S.E.M.

The inhibition constant Ki is approximately equal to the concentration of the adamantane in nM required to displace 50% of the MK-801 specifically bound to the receptor. In this regard, memantine (Compound No. 1) was found to be the most potent compound subjected to this test, when compared with thirteen (13) other clinically-used and centrally-acting drugs, as reported in the foregoing publication.

The invention is further described by the following illustrative examples, which are not to be construed as limiting:

EXAMPLE 1

Injectable Solution

For preparing a 0.5% solution, dissolve 0.5% active ingredient and 0.8% sodium chloride (DAB 9) in doubly distilled water. Filter the solution through an antimicrobial filter, fill into 2-ml ampoules and sterilize for 20 minutes at 120° C. in an autoclave.

EXAMPLE 2

Solution

Dissolve 1% of active agent in demineralized water. Filter the solution before filling.

EXAMPLE 3

Tablets

| 1 tablet contains: | |
|---|---|
| Active ingredient | 10.0 mg |
| Lactose | 67.5 mg |
| Microcrystalline cellulose | 18.0 mg |
| Talc | 4.5 mg |
| | 100.0 mg |

The substances are mixed and the mixture compressed into 100-mg tablets in a direct tableting procedure without granulation.

EXAMPLE 4

Coated Tablets

Prepare 6-mm tablet cores of 100 mg as described under "Tablets". Coat the tablets in a sugar-coating process by coating the core with a sugar suspension first, followed by staining with a colored syrup and polishing.

The tablet coating consists of:

| Sugar | 65.0 mg |
|---|---|
| Talc | 39.0 mg |
| Calcium carbonate | 13.0 mg |
| Gum arabic | 6.5 mg |
| Corn starch | 3.7 mg |
| Shellac | 1.1 mg |
| Polyethylene glycol 6000 | 0.2 mg |
| Magnesia usta | 1.3 mg |
| Dye | 0.2 mg |
| | 130.0 mg |

Total tablet weight: 230 mg

EXAMPLE 5

For preparing a 0.01% infusion solution, dissolve 0.01% of active ingredient and 5% levulose in doubly-distilled water. Filter the solution through an antimicrobial filter, fill into 500-ml infusion bottles, and sterilize.

The example provides 50 mg of active substance per single dose.

EXAMPLE 6

Synthesis of 1-Amino-3-isopropyl Adamantane Hydrochloride (Test Compound No. 3)

A. Preparation of Adamantane Methyl Carboxylate (I)

Stir 1.0 mol of adamantane carboxylic acid in 600 ml of methanol. Under ice cooling, drop 1.53 mol of acetyl chloride into the solution within 1 h. Remove the ice bath, and allow the reaction mixture to reach room temperature. Subsequently, heat for 3 hrs under reflux. Evaporate the reaction mixture to dryness under vacuum and distill. (Yield: 97%).

B. Preparation of Isopropyl Adamantane (II)

Introduce 0.5 mol of magnesium chips into 50 ml of absolute ether, and drop 0.5 mol of methyl iodide into the solution under moisture-free conditions until the ether boils. Subsequently, heat in a water bath until the magnesium has completely dissolved. Into this solution at room temperature drop 0.2 mol of adamantane methyl carboxylate in absolute ether. Then heat to reflux for 3 hours. After cooling, hydrolize with ice and mix with ammonium chloride solution until the precipitate has dissolved. Separate the ether phase, wash the aqueous phase with 2 portions of ether, and wash the combined organic phases with sodium bicarbonate solution. Then dry and evaporate to dryness under vacuum. (Yield: 93%).

C. Preparation of Isopropene Adamantane (III)

Stir 0.25 mol of isopropyl adamantane (II) in 500 ml acetic anhydride for 12 hours at 160° C. Subsequently, pour the reaction mixture onto 1 liter of ice water and extract with ether. Dry the combined organic phases with magnesium sulfate, filter, and evaporate to dryness under vacuum. Distill the residue under vacuum. (Yield: 66%).

D. Preparation of Isopropyl Adamantane (IV)

Dissolve 0.074 mol of adamantyl isopropene (III) in 100 ml of absolute ethanol. Add 4 g of palladium (5% on activated carbon) and hydrate under stirring for 24 hrs at room temperature. Subsequently, filter off the catalyst, and remove the solvent under vacuum. (Yield: 91%).

E. Preparation of 1-Bromo-3-isopropyl Adamantane (V)

Mix 0.034 mol of isopropyl adamantane (IV) with a ten times excess of bromine (0.33 mol). Heat slowly and stir under reflux for 4 h. Subsequently, allow to cool and pour onto ice water. Decompose the excess bromine with sodium sulfite until the aqueous solution has discolored. Then extract with ether, wash the combined organic phases with sodium bicarbonate solution, dry with magnesium sulfate, filter and evaporate to dryness under vacuum. Recrystallize the residue from methanol. (Yield: 83%).

F. Preparation of 1-N-formyl-3-isopropyl Adamantane (VI)

Heat 0.028 mol of 1-bromo-3-isopropyl adamantane (V) with 40 ml of formamide to reflux for 12 hrs. After cooling, pour the reaction mixture onto water and extract with dichloromethane. Dry the combined organic phases with magnesium sulfate, filter and evaporate to dryness under vacuum. (Yield: 82%).

G. Preparation of 1-Amino-3-isopropyl Adamantane Hydrochloride

Mix 0.023 mol of 1-N-formyl-3-isopropyl adamantane (VI) with 100 ml of 15% hydrochloric acid and heat to boiling for 24 hrs. After cooling, filter the precipitate and recrystallize from isopropanol. (Yield: 57%).

EXAMPLE 7

Synthesis of 1-Amino-3-cyclohexyl Adamantane Hydrochloride (Test Compound No. 7)

A. Preparation of 1-Phenyl Adamantane (I)

Heat 0.068 mol of iron(III) chloride to boiling in 20 ml of absolute benzene. Drop 0.0186 mol of 1-bromoadamantane, dissolved in 30 ml of absolute benzene, to the solution. Then heat to boiling for 3 hrs. After cooling, pour the reaction mixture onto ice/hydrochloric acid, separate the organic phase, and extract the aqueous phase with two portions of benzene. Wash the combined organic phases with water, dry with calcium chloride, filter and evaporate to dryness under vacuum. Recrystallize the residue from methanol. (Yield: 80%).

B. Preparation of 1-Hydroxy-3-phenyl Adamantane (II)

To a solution of 0.03 mol chromiumtrioxide in 20 ml glacial acetic acid and 20 ml acetic anhydride, add 0.0095 mol of 1-phenyl adamantane at 0° C. and stir for 24 hours at 4° C. Pour the reaction mixture onto water and extract with three portions of pentane. Wash the organic phase with saturated sodium chloride solution, dry over magnesium sulfate, filter and evaporate to dryness under vacuum. Hydrolize the residue with 20 ml of 2N NaOH and 50 ml of methanol. Subsequently, remove the methanol under vacuum and dilute the residue with water. Then extract with three portions of ether. Dry the organic phase, filter and evaporate to dryness under vacuum. Recrystallize the residue from cyclohexane. (Yield: 50%).

Ref.: H. Stetter, M. Schwarz, A. Hirschhorn, Chem. Ber. (1959), 92, 1629–35.

C. Preparation of 1-Bromo-3-phenyl Adamantane (III)

Stir 0.03 mol of 3-phenyl adamantanol (II) with 100 ml of 40% HBr in glacial acetic acid for 20 min at 60° C. and 30 min at room temperature. Subsequently, dilute the reaction mixture with water and extract with ether. Wash the combined organic extracts with sodium chloride solution, dry with magnesium sulfate, filter and evaporate to dryness under vacuum. Recrystallize the residue from methanol. (Yield: 68%).

Ref.: W. Fischer, C. A. Grog, Helvetica Chim. Acta (1976), 59, 1953.

D. Preparation of 1-N-formyl-3-phenyl Adamantane (IV)

Heat 0.03 mol of 1-bromo-3-phenyl adamantane (III) with 50 ml of formamide for 12 hrs to reflux. After cooling, pour the reaction mixture onto water and extract with dichloromethane. Dry the combined organic phases with magnesium sulfate, filter and evaporate to dryness under vacuum. (Yield: 80%).

E. Preparation of 1-Amino-3-phenyl Adamantane Hydrochloride (V)

Heat 0.02 mol of 1-N-formyl-3-phenyl adamantane (IV) with 100 ml of 15% hydrochloric acid at reflux for 24 hours. After cooling, filter the precipitate and recrystallize from isopropanol. (Yield: 60%).

F. Preparation of 1-Amino-3-cyclohexyl Adamantane (VI)

Dissolve 0.011 mol of 1-amino-3-phenyl adamantane (V) in 150 ml glacial acetic acid, mix with 0.3 g of platinum oxide (1% on activated carbon) and hydrate in a Parr apparatus at 35° C. at a hydrogen pressure of 3 bar. Subsequently, remove the catalyst by filtration and evaporate the filtrate to dryness. Take up the residue in methanol and precipitate the product with ether. Suck off and dry. (Yield: 70%).

EXAMPLE 8

Synthesis of 1-Amino-3,5-dimethyl-7-ethyl Adamantane Hydrochloride (Test Compound No. 8)

A. Preparation of 1-Bromo-3,5-dimethyl Adamantane (I)

Mix 0.5 mol of 1,3-dimethyl adamantane with a ten times excess of bromine (5 mol). Slowly heat and stir for 4 hrs under reflux. Subsequently, allow to cool and pour onto ice water. Decompose the excess bromine with sodium sulfite until discoloration of the aqueous solution. Then extract with ether, wash the combined organic phases with sodium bicarbonate solution, dry with magnesium sulfate, filter and evaporate to dryness under vacuum. Recrystallize the residue from methanol. (Yield: 83%).

B. Preparation of 1-(2-Bromoethyl)-3,5-dimethyl Adamantane (II)

Mix 1.4 mol of 1-bromo-3,5-dimethyl adamantane (I) in hexane with 0.6 mol of aluminum bromide at −75° C. Subsequently, pass ethylene through the solution for 20-30 minutes, stir for 5 min., and pour the reaction mixture onto ice water. Extract with ether, dry the organic phase and evaporate to dryness. Recrystallize the residue from methanol. (Yield: 48%).

C. Preparation of 1,3-Dimethyl-5-ethyl Adamantane (III)

Dissolve 0.5 mol of 1-(2-bromoethyl)-3,5-dimethyl adamantane (II) in toluene, mix with 0.55 mol of sodium-bis(2-methoxy-ethoxy)dihydro aluminate, and heat to boiling for 3 hrs. After hydrolysis, separate the organic phase, dry with magnesium sulfate, and evaporate to dryness under vacuum. Purify the residue by vacuum distillation. (Yield: 86%).

D. Preparation of 1-Bromo-3,5-dimethyl-7-ethyl Adamantane (IV)

Mix 0.4 mol of 1,3-dimethyl-5-ethyl adamantane (III) with a ten times excess of bromine (4 mol). Heat slowly and stir for 4 hrs under reflux. Subsequently allow to cool and pour onto ice water. Decompose the excess bromine with sodium sulfite until discolouration of the aqueous solution. Then extract with ether, wash the combined organic phases with sodium bicarbonate solution, dry with magnesium sulfate, filter and evaporate to dryness under vacuum. Recrystallize the residue from methanol. (Yield: 86%).

E. Preparation of 1-N-formyl-3,5-dimethyl-7-ethyl Adamantane (V)

Heat 0.2 mol of 1-bromine-3,5-dimethyl-7-ethyl adamantane (IV) with 150 ml of formamide at reflux for 12 hrs. After cooling, pour the reaction mixture onto water and extract with dichloromethane. Dry the combined organic phases with magnesium sulfate, filter and evaporate to dryness under vacuum. (Yield: 82%).

F. Preparation of 1-Amino-3,5-dimethyl-7-ethyl Adamantane Hydrochloride (VI)

Mix 0.2 mol of 1-N-formyl-3,5-dimethyl-7-ethyl adamantane (V) with 100 ml of 15% hydrochloric acid and heat to boiling for 24 hrs. After cooling, filter the precipitate and recrystallize from isopropanol. (Yield: 57%).

EXAMPLE 9

Synthesis of 1-N-methylamino-3,5-dimethyl Adamantane (Test Compound No. 5)

Dissolve 0.1 mol of the appropriately substituted amino adamantane (1-amino-3,5-dimethyl adamantane) with 0.15 mol of chloromethyl formate and potassium carbonate in acetone and heat to reflux for 8 hrs. After cooling, filter the solution, remove the solvent and dry the residue. Mix the raw product (0.05 mol) with 0.1 mol of sodium-bis-(2-methoxy-ethoxy)-dihydro aluminate in toluene and heat at reflux for 3 hrs. After cooling, hydrolize with dilute HCl, dry the organic phase and evaporate to dryness. Purify the raw material by distillation.

EXAMPLE 10

Synthesis of 1-Amino-3-ethyl-5-phenyl Adamantane

A. Preparation of 1-Bromo-3-ethyl Adamantane (I)

Mix 0.034 mol of ethyl adamantane with a ten times excess of bromine (0.33 mol). Heat slowly and stir under reflux for 4 hrs. Then allow to cool and pour onto ice water. Decompose the excess bromine with sodium sulfite until discoloration of the aqueous solution. Subsequently extract with ether, wash the combined organic phases with sodium bicarbonate solution, dry with magnesium sulfate, filter and evaporate to dryness under vacuum. Recrystallize the residue from methanol. (Yield: 83%).

B. Preparation of 1-Ethyl-3-phenyl Adamantane (II)

Heat 0.068 mol of iron(III) chloride in 20 ml of absolute benzene to boiling. Drop 0.0186 mol of 1-bromo-3-ethyl adamantane (I), dissolved in 30 ml of absolute benzene, into the solution. Then heat at reflux for 3 hrs. After cooling, pour the reaction mixture onto ice/hydrochloric acid, separate the organic phase, and extract with two portions of benzene. Wash the combined organic phases with water, dry with calcium chloride, filter and evaporate to dryness. Recrystallize the residue from methanol. (Yield: 80%).

C. Preparation of 1-Ethyl-3-hydroxy-5-phenyl Adamantane (III)

To a solution of 0.03 mol of chromiumtrioxide, in 20 ml glacial acetic acid and 20 ml acetic anhydride, add 0.0095 mol of 1-ethyl-3-phenyl adamantane (II) at 0° C. and stir for 24 hours at 4° C. Pour the reaction mixture into water and extract with three portions of pentane. Wash the organic phase with saturated sodium chloride solution, dry over magnesium sulfate, filter and evaporate to dryness under vacuum. Hydrolize the residue with 20 ml of 2N NaOH and 50 ml of methanol. Remove the methanol under vacuum and dilute the residue with water. Then extract with three portions of ether. Dry the organic phase, filter and evaporate to dryness under vacuum. Recrystallize the residue from cyclohexane. (Yield: 50%).

Ref.: H. Stetter, M. Schwarz, A. Hirschhorn, Chem. Ber. (1959), 92, 1629-35.

D. Preparation of 1-Bromo-3-ethyl-5-phenyl Adamantane (IV)

Stir 0.03 mol of 1-ethyl-3-hydroxy-5-phenyl adamantane (III) with 100 ml of 40% HBr in glacial acetic acid for 20 min at 60° C. and for 30 min at room temperature. Subsequently dilute the reaction mixture with water and extract with ether. Wash the combined organic extracts with sodium chloride solution, dry with magnesium sulfate, filter and evaporate to dryness under vacuum. Recrystallize the residue from methanol. (Yield: 68%).

Ref.: W. Fischer, C. A. Grog, Helvetica Chim. Acta (1976), 59, 1953.

E. Preparation of 1-N-formyl-3-ethyl-5-phenyl Adamantane (V)

Heat 0.03 mol of 1-ethyl-3-hydroxy-5-phenyl adamantane (IV) with 50 ml of formamide for 12 hrs at reflux. After cooling, pour the reaction mixture into water and extract with dichloromethane. Dry the combined organic phases with magnesium sulfate, filter and evaporate to dryness. (Yield: 80%).

F. Preparation of 1-Amino-3-ethyl-5-phenyl Adamantane Hydrochloride (VI)

Heat 0.02 mol of 1-N-formyl-3-ethyl-5-phenyl adamantane (V) with 100 ml of 15% hydrochloric acid for 24 hrs at reflux. After cooling, filter the precipitate and recrystallize from isopropanol. (Yield: 60%).

It is thus seen that certain adamantane derivatives, some of which are novel, have been provided for the prevention and treatment of cerebral ischemia, and that pharmaceutical compositions embodying such an adamantane derivative have been provided for use in the prevention and treatment of cerebral ischemia, the amount of the said adamantane derivative provided in either case being a cerebral ischemia-alleviating or preventive amount.

Various modifications and equivalents will be apparent to one skilled in the art and may be made in the compounds, compositions, methods, and procedures of the present invention without departing from the spirit or scope thereof, and it is therefore to be understood that the invention is to be limited only by the full scope which can be legally attributed to the appended claims.

We claim:

1. A method for the prevention or treatment of cerebral ischemia comprising the step of administering, to a patient in need thereof, an effective amount of an adamantane derivative of the general formula

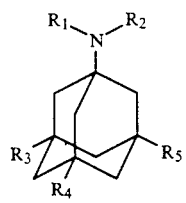

wherein
$R_1$ and $R_2$ are identical or different and represent hydrogen or a straight or branched alkyl group of 1 to 6 C atoms or, in conjunction with N, a heterocyclic group with 5 or 6 ring C atoms;
wherein
$R_3$ and $R_4$ are identical or different, being selected from hydrogen, a straight or branched alkyl group of 1 to 6 C atoms, a cycloalkyl group with 5 or 6 C atoms, and phenyl;
wherein
$R_5$ is hydrogen or a straight or branched $C_1$–$C_6$ alkyl group,
or a pharmaceutically-acceptable salt thereof.

2. A method according to claim 1, wherein $R_1$, $R_2$ and $R_5$ are hydrogen.

3. A method according to claim 2, wherein $R_1$, $R_2$ and $R_5$ are hydrogen, and $R_3$ and $R_4$ are methyl.

4. A method according to claim 2, wherein $R_1$, $R_2$ and $R_5$ are hydrogen, and $R_3$ and $R_4$ are ethyl.

5. A method according to claim 1, wherein $R_1$, $R_2$, $R_4$ and $R_5$ are hydrogen, and $R_3$ is ethyl, isopropyl, or cyclohexyl.

6. A method according to claim 1, wherein $R_2$ and $R_5$ are hydrogen.

7. A method according to claim 6, wherein $R_3$ and $R_4$ are methyl, $R_2$ and $R_5$ are hydrogen and $R_1$ is methyl or ethyl.

8. A method according to claim 1, wherein $R_1$ and $R_2$ are hydrogen.

9. A method according to claim 8, wherein $R_1$ and $R_2$ are hydrogen, $R_3$ is ethyl, and $R_5$ and $R_4$ are methyl.

10. A method according to claim 1 for the treatment of Alzheimer's disease.

11. A method of claim 1, wherein the adamantane derivative is administered in an effective cerebral ischemia-alleviating or preventive amount.

12. A method of claim 11, wherein the adamantane derivative is administered in the form of a composition containing the same together with a pharmaceutically-acceptable carrier or diluent.

13. A method of claim 11, wherein the adamantane derivative is administered in an amount effective to prevent degeneration and loss of nerve cells after ischemia.

* * * * *

UNITED STATES PATENT AND TRADEMARK OFFICE
CERTIFICATE OF CORRECTION

PATENT NO. : 5,061,703 C1
APPLICATION NO. : 90/007176
DATED : November 7, 2006
INVENTOR(S) : Joachim Bormann et al.

It is certified that error appears in the above-identified patent and that said Letters Patent is hereby corrected as shown below:

Claim 1, line 56: delete "wherein" and substitute --*wherein*--.

Claim 1, line 57: delete "$R_4$ *and*" and substitute --$R_4$, *and*--.

Claim 1, line 58: delete "*simultaneously;*" and substitute --*simultaneously,*--.

Claim 10, line 62: delete "disease *wherein*" and substitute --disease, *wherein*--.

Claim 18, line 64: delete "in" and substitute --is--.

Signed and Sealed this

Fifth Day of June, 2007

JON W. DUDAS
*Director of the United States Patent and Trademark Office*

(12) EX PARTE REEXAMINATION CERTIFICATE (5595th)
United States Patent
Bormann et al.

(10) Number: US 5,061,703 C1
(45) Certificate Issued: Nov. 7, 2006

(54) ADAMANTANE DERIVATIVES IN THE PREVENTION AND TREATMENT OF CEREBRAL ISCHEMIA

(75) Inventors: Joachim Bormann, Frankfurt (DE); Markus R. Gold, Nauheim (DE); Wolfgang Schatton, Eschborn (DE)

(73) Assignee: Merz Pharma GmbH & Co. KGaA, Frankfurt am Main (DE)

Reexamination Request:
No. 90/007,176, Aug. 18, 2004

Reexamination Certificate for:
Patent No.: 5,061,703
Issued: Oct. 29, 1991
Appl. No.: 07/508,109
Filed: Apr. 11, 1990

(30) Foreign Application Priority Data

Apr. 14, 1989 (EP) .......................................... 89106657

(51) Int. Cl.
*A61K 31/55* (2006.01)
*A61K 31/445* (2006.01)
*A61K 31/41* (2006.01)

(52) U.S. Cl. .................. 514/212.01; 514/325; 514/359
(58) Field of Classification Search ............ 514/212.01, 514/325, 359
See application file for complete search history.

(56) References Cited

U.S. PATENT DOCUMENTS 3,450,761 A    6/1969    Schneider

FOREIGN PATENT DOCUMENTS

EP    0293974    12/1988
JP    58-4718    1/1983

OTHER PUBLICATIONS

Translation of: Rote Liste 63 008 (1983).
Translation of: Rote Liste 63 009 (1984).
Translation of: Rote Liste 63 008 (1985).
Translation of: Rote Liste 63 005 (1987).
Translation of: Rote Liste 63 005 (1988).
Translation of: Rote Liste 63 006 (1989).
Translation of: Akatinol® Memantine Labeling (Apr. 1984).
Translation of: Akatinol® Memantine Labeling (Feb. 1988).
Translation of: Pschyrembel Klinisches Worterbuch [Clinical Dictionary] 1839–1840 (255$^{th}$ ed. 1986).
Translation of: Pschyrembel Klinisches Worterbuch [Clinical Dictionary] 1384 (255$^{th}$ ed. 1986).
Translation of: Pschyrembel Klinisches Worterbuch [Clinical Dictionary] 808 (255$^{th}$ ed. 1986).
Translation of: Deutsche medizinische Wochenschrift [German Medical Weekly] 109: 987–990 (1984).
Fünfgeld et al., Psychopharmacology, XVI$^{th}$ C.I.N.P. Congress, Munich, 27.23.08, p. 180 (Aug. 15–18, 1988).
Adolfsson et al., Aging vol. 7, pp. 441–451 (1978).
Castaigne et al., La Nouvelle Presse Médicale, *Etude clinique de l'action psycho–stimulante de l'amantadine,* 3(26):1663–1664 (Jun. 29, 1974).
Costall B. and Naylor R.J. (1975). Neuropharmacological studies on D 145 (1,3 dimethyl–5–aminoadamantan). Psychopharmacologia (Berl.) 43:53–61.
Fischer P.A., Jacobi R., Scheider E. and Schonberger B. (1977). Die Wirkung Intravenoser Gaben von Memantin bei Parkinson–Kranken. Arzneim. Forsch./Drug. Res. 27 (II) Nr. 7, 1487.
Maj J., Sowinska H., Baran L. and Samek J. (1974). Pharmacological effects of 1,3–dimethyl–5–aminoadamantane, a new Adamantane derivative. Europ. J. Pharmacology 26, 9–14.
Schubert & Fleischhacker, Arztliche Praxis, XXXI, No. 46, vol. 9, pp. 2157–2160 (Jun. 1979).
Erkulwater and Pillai, Southern Med. J., 82: 550–553 (May 1989).
Moos, Medicinal Research Reviews; 8: 353–91 (1988).
Sieb et al., Dtch. Med. Wschr.; 112: 769–72 (1987).
Danielczyk, Psychiatria Danubina; 1: 71–75 (1989).
Kugler, Munich. Med. Wschr.; 127: 974–77 (1985).
Stetzer, Med. Welt; 35: 291–295 (Mar. 2, 1984).
Wallnofer and Schiller, Med. Welt.; 25: 703–706 (1974).
Pandeya, Indian J. Pharmacy.; 33: 1–9 (Jan.–Feb. 1971).
Bruseghini et al., II$^e$ renunion luso–espagnole de pharmacologie, II Congreso Nacitonal de Quimica Terapeutica; Madrid (1982).

(Continued)

*Primary Examiner*—Kevin E. Weddington

(57) ABSTRACT

A method for the prevention and treatment of cerebral ischemia using an adamantane derivative of the formula

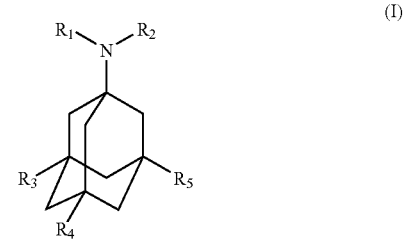

(I)

wherein
 $R_1$ and $R_2$ are identical or different, representing hydrogen or a straight or branched alkyl group of 1 to 6 C atoms or, in conjunction with N, a heterocyclic group with 5 or 6 ring C atoms;
wherein
 $R_3$ and $R_4$ are identical or different, being selected from hydrogen, a straight or branched alkyl group of 1 to 6 C atoms, a cycloalkyl group with 5 or 6 C atoms, and phenyl;
wherein
 $R_5$ is hydrogen or a straight or branched $C_1$-$C_6$ alkyl group,
or a pharmaceutically-acceptable salt thereof, is disclosed.

OTHER PUBLICATIONS

Burkhard et al., Institute of Chemical Technology Prague, pp. 91–97 (1973).
Meldrum et al., Naunyn–Schmiedeberg's Arch Pharmacol, 332:93–97 (1986).
Chojnacka–Wojcik et al., Pol. J. Pharmacol. Pharm. 35: 511–515 (1983).
Falbe et al., Rompp Chemie Lexikon, pp. 141, 151 (1989).
Berkow, Merck Manual, 14th ed. pp. 1324–1331(1982).
Otomo, Journal of Clinical Medicine, 7:127–132 (1988).
Tempel, D. Therapiewoche, 39 (14): 946–952 (Apr. 2, 1989).
Schäfer & Thiery, Psycho, 10:851–852 (1984).
Fröstl & Maitre, Pharmacopsychiat., 22: 54–100 (Supplement) (1989).
Koch, "Pharmakologie von Memantine" (1987).
Zimmerman, "Memantine—Ein neues Prinzip in der Geriatrie" (1987).
Tempel, "Ergebnisse einer Pilotuntersuchung mit zwei Dosisstufen von Memantine in der Geriatrie" (1988).
Tempel, "Memantine—Klinische Prüfungen in der Geriatrie" (1987).
Marcea, "Kooperationsmöglichkeiten zwischen Klinik und niedergelassenen Ärzten bei der Rehabilitation von Alterspatientien" (1987).
Rote Liste 63 008 (1983).
Rote Liste 63 009 (1984).
Rote Liste 63 008 (1985).
Rote Liste 63 005 (1987).
Rote Liste 63 005 (1988).
Rote Liste 63 006 (1989).
Akatinol® Memantine Labeling (Apr. 1984).
Akatinol® Memantine Labeling (Feb. 1988).
Pschyrembel Klinisches Worterbuch [Clinical Dictionary] 1839–1840 ($255^{th}$ ed. 1986).
Pschyrembel Klinisches Worterbuch [Clinical Dictionary] 1384 ($255^{th}$ ed. 1986).
Pschyrembel Klinisches Worterbuch [Clinical Dictionary] 808 ($255^{th}$ ed. 1986).
Olney et al., *European Journal of Pharmacology* 142:319–320 (1987).
Deutsche medizinische Wochenschrift [German Medical Weekly] 109: 987–990 (1984).
SCIENCE, vol. 226, pp. 850–852 (1984).
Cotman et al., Annual Review of Neuroscience, 11:61–80 (1988).
Rothman & Olney, Annals of Neurology, 19(2):108 (Feb. 1986).
Kemp et al., TINS, 10(7):294–298 (1987).
EP Application No. 89106657 (originally filed application for EP 0392059).
Response from Merz to EPO on Feb. 6, 1992.
EPO Examination Report dated Oct. 21, 1991.
Katzman, Alzheimer's Disease: Senile Dementia and Related Disorders, vol. 7, pp. 197–211 (1978).
Hahn et al., *Proc. Natl. Acad. Sci.,* 85:6556–6560 (1988).
Ingvar et al., Aging vol. 70, pp. 203–211 (1978).
Rote Liste, 63 008 (1986).
Marcea et al. Therapiewoche, 38:3097–3100 (1988).
Fleischhacker et al., Progress in Neuro–Psychopharmacology & Biological Psychiatry, 10:87–93 (1986).
Ambrozi et al., Pharmacopsychiatry, 21:144–146 (1988).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 10 are determined to be patentable as amended.

Claims 2–9 and 11–13, dependent on an amended claim, are determined to be patentable.

New claims 14–19 are added and determined to be patentable.

1. A method for the prevention or treatment of cerebral ischemia comprising the step of *orally* administering, to a patient *diagnosed with Alzheimer's disease and* in need thereof, an effective amount of an adamantane derivative of the general formula

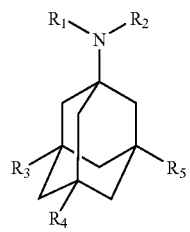

wherein $R_1$ and $R_2$ are identical or different and represent hydrogen or a straight or branched alkyl group of 1 to 6 C atoms or, in conjunction with N, a heterocyclic group with 5 or 6 ring C atoms;

wherein $R_3$ and $R_4$ are identical or different, being selected from hydrogen, a straight or branched alkyl group of 1 to 6 C atoms, a cycloalkyl group with 5 or 6 C atoms, and phenyl;

wherein $R_5$ is hydrogen or a straight or branched $C_1$–$C_6$ alkyl group; *and* wherein

*$R_1$, $R_2$, $R_3$, $R_4$ and $R_5$ do not all represent hydrogen simultaneously;* or a pharmaceutically-acceptable salt thereof.

10. A method according to claim 1 for the treatment of Alzheimer's disease *wherein said adamantane derivative is memantine and said effective amount is from about 0.01 to 100 mg/kg*.

*14. A method for the treatment of cerebral ischemia comprising orally administering to a patient diagnosed with Alzheimer's disease and in need of such treatment an effective amount of an adamantane derivative of the general formula*

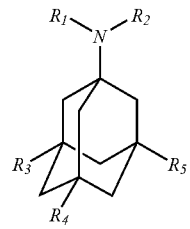

*wherein*

*$R_1$ and $R_2$ are identical or different and represent hydrogen or a straight or branched alkyl group of 1 to 6 C atoms or, in conjunction with N, a heterocyclic group with 5 or 6 ring C atoms;*

*wherein*

*$R_3$ and $R_4$ are identical or different, being selected from hydrogen, a straight or branched alkyl group of 1 to 6 C atoms, a cycloalkyl group with 5 or 6 C atoms, and phenyl;*

*wherein*

*$R_5$ is hydrogen or a straight or branched $C_1$–$C_6$ alkyl group; and*

*wherein*

*$R_1$, $R_2$, $R_3$, $R_4$, and $R_5$ do not all represent hydrogen simultaneously,*

*or a pharmaceutically-acceptable salt thereof.*

*15. The method of claim 14, wherein said adamantane derivative is memantine.*

*16. The method of claim 14, wherein said effective amount is from about 0.01 to 100 mg/kg.*

*17. A method for the treatment of an imbalance of neuronal stimulation after Alzheimer's disease, comprising orally administering to a patient diagnosed with Alzheimer's disease and in need of such treatment an effective amount of an adamantane derivative of the general formula*

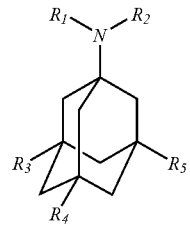

*wherein*

*$R_1$ and $R_2$ are identical or different and represent hydrogen or a straight or branched alkyl group of 1 to 6 C atoms or, in conjunction with N, a heterocyclic group with 5 or 6 ring C atoms;*

*wherein*

*$R_3$ and $R_4$ are identical or different, being selected from hydrogen, a straight or branched alkyl group of 1 to 6 C atoms, a cycloalkyl group with 5 or 6 C atoms, and phenyl;*

*wherein*

*$R_5$ is hydrogen or a straight or branched $C_1$–$C_6$ alkyl group; and*

*wherein*

*$R_1$, $R_2$, $R_3$, $R_4$, and $R_5$ do not all represent hydrogen simultaneously,*

*or a pharmaceutically-acceptable salt thereof.*

*18. The method of claim 17, wherein said adamantane derivative in memantine.*

*19. The method of claim 17, wherein said effective amount is from about 0.01 to 100 mg/kg.*

* * * * *